(12) United States Patent
Tuan

(10) Patent No.: US 7,866,819 B2
(45) Date of Patent: Jan. 11, 2011

(54) NON-INVASIVE MEASUREMENT OF TEAR VOLUME SYSTEMS AND METHODS

(75) Inventor: Kuang-Mon Ashley Tuan, Castro Valley, CA (US)

(73) Assignee: AMO Manufacturing USA, LLC., Santa Ana, CA (US)

( * ) Notice: Subject to any disclaimer, the term of this patent is extended or adjusted under 35 U.S.C. 154(b) by 0 days.

(21) Appl. No.: 12/403,229

(22) Filed: Mar. 12, 2009

(65) Prior Publication Data

US 2009/0168019 A1 Jul. 2, 2009

Related U.S. Application Data

(63) Continuation of application No. 11/335,861, filed on Jan. 18, 2006, now Pat. No. 7,520,609.

(51) Int. Cl.
*A61B 3/14* (2006.01)
*A61B 3/10* (2006.01)

(52) U.S. Cl. ........................ 351/206; 351/212

(58) Field of Classification Search ........... 351/200, 351/205–206, 208, 212
See application file for complete search history.

(56) References Cited

U.S. PATENT DOCUMENTS

| | | | |
|---|---|---|---|
| 4,665,913 A | 5/1987 | L'Esperance | |
| 4,669,466 A | 6/1987 | L'Esperance | |
| 4,732,148 A | 3/1988 | L'Esperance | |
| 4,747,683 A | 5/1988 | Doane | |
| 4,770,172 A | 9/1988 | L'Esperance | |
| 4,773,414 A | 9/1988 | L'Esperance | |
| 5,108,388 A | 4/1992 | Trokel | |
| 5,144,630 A | 9/1992 | Lin | |
| 5,163,934 A | 11/1992 | Munnerlyn | |
| 5,207,668 A | 5/1993 | L'Esperance | |

(Continued)

FOREIGN PATENT DOCUMENTS

EP 0 943 288 A1 9/1999

(Continued)

OTHER PUBLICATIONS

Yokoi et al., Reflective meniscometry: a non-invasive method to measure tear meniscus curvature, Br. J. Ophthalmology (1999) 83:92-97.

(Continued)

*Primary Examiner*—Scott J Sugarman
*Assistant Examiner*—Dawayne A Pinkney

(57) ABSTRACT

Devices systems, and methods can measure, diagnose and/or characterize an eye of a patient, including physiologic and optical properties, such as hydration and tear volume in relation to an optical surface of the eye, including topography of a corneal surface of the eye and/or a wavefront elevation map of the eye. The system forms an image of a tear meniscus along an eyelid. The eye can be illuminated so that the meniscus appears as a dark band in the image. Tear volume can be determined by measuring a height across the tear meniscus. The tear volume can be used to determine the optical properties of the tear of the eye and to diagnose conditions of the eye. The patient can be screened for treatment of the eye with refractive surgery using a measured pupil size, hydration and topography and/or wavefront.

16 Claims, 10 Drawing Sheets

U.S. PATENT DOCUMENTS

| | | | |
|---|---|---|---|
| 5,219,343 | A | 6/1993 | L'Esperance |
| 5,520,679 | A | 5/1996 | Lin |
| 5,646,791 | A | 7/1997 | Glockler |
| 5,742,626 | A | 4/1998 | Mead |
| 5,782,822 | A | 7/1998 | Telfair |
| 5,963,300 | A | 10/1999 | Horwitz |
| 6,004,313 | A | 12/1999 | Shimmick |
| 6,050,687 | A | 4/2000 | Bille |
| 6,090,102 | A | 7/2000 | Telfair |
| 6,095,651 | A | 8/2000 | Williams |
| 6,236,459 | B1 | 5/2001 | Negahdaripour et al. |
| 6,271,915 | B1 | 8/2001 | Frey |
| 6,447,119 | B1 * | 9/2002 | Stewart et al. ............ 351/212 |
| 6,659,613 | B2 | 12/2003 | Applegate et al. |
| 6,685,320 | B2 | 2/2004 | Hirohara et al. |
| 7,278,740 | B1 | 10/2007 | Suzuki et al. |
| 7,281,801 | B2 | 10/2007 | Wang |
| 7,520,609 | B2 | 4/2009 | Tuan |
| 2003/0038921 | A1 | 2/2003 | Neal et al. |
| 2004/0070730 | A1 | 4/2004 | Mihashi et al. |
| 2004/0212781 | A1 | 10/2004 | Mihashi |
| 2005/0105044 | A1 | 5/2005 | Warden et al. |
| 2006/0109423 | A1 * | 5/2006 | Wang ........................ 351/206 |

FOREIGN PATENT DOCUMENTS

| | | |
|---|---|---|
| EP | 1 364 612 A1 | 11/2003 |
| WO | WO 01/08547 A | 2/2001 |
| WO | WO 02/11612 A2 | 2/2002 |

OTHER PUBLICATIONS

Dubra et al., "Double lateral shearing interferometer for the quantitative measurement of tear film topography," Applied Optics, Mar. 1, 2005;44(7):1191-1199.

Erdélyi et al., "Spontaneous alterations of the corneal topographic pattern," J Cataract Refract Surg. May 2005;31(5):973-978.

Mainstone et al: "Tear meniscus measurement in the diagnosis of dry eye" Curr Eye Res. Jun. 1996;15(6):653-661.

Zhou et al., Validation of a combined corneal topographer and aberrometer based on Shack-Hartmann wave-front sensing J Opt Soc Am A Opt Image Sci Vis. May 2004;21(5):683-696.

European Search Report and Search Opinion of EP Patent Application No. 06850336.6, mailed Nov. 24, 2009, 14 pages total.

* cited by examiner

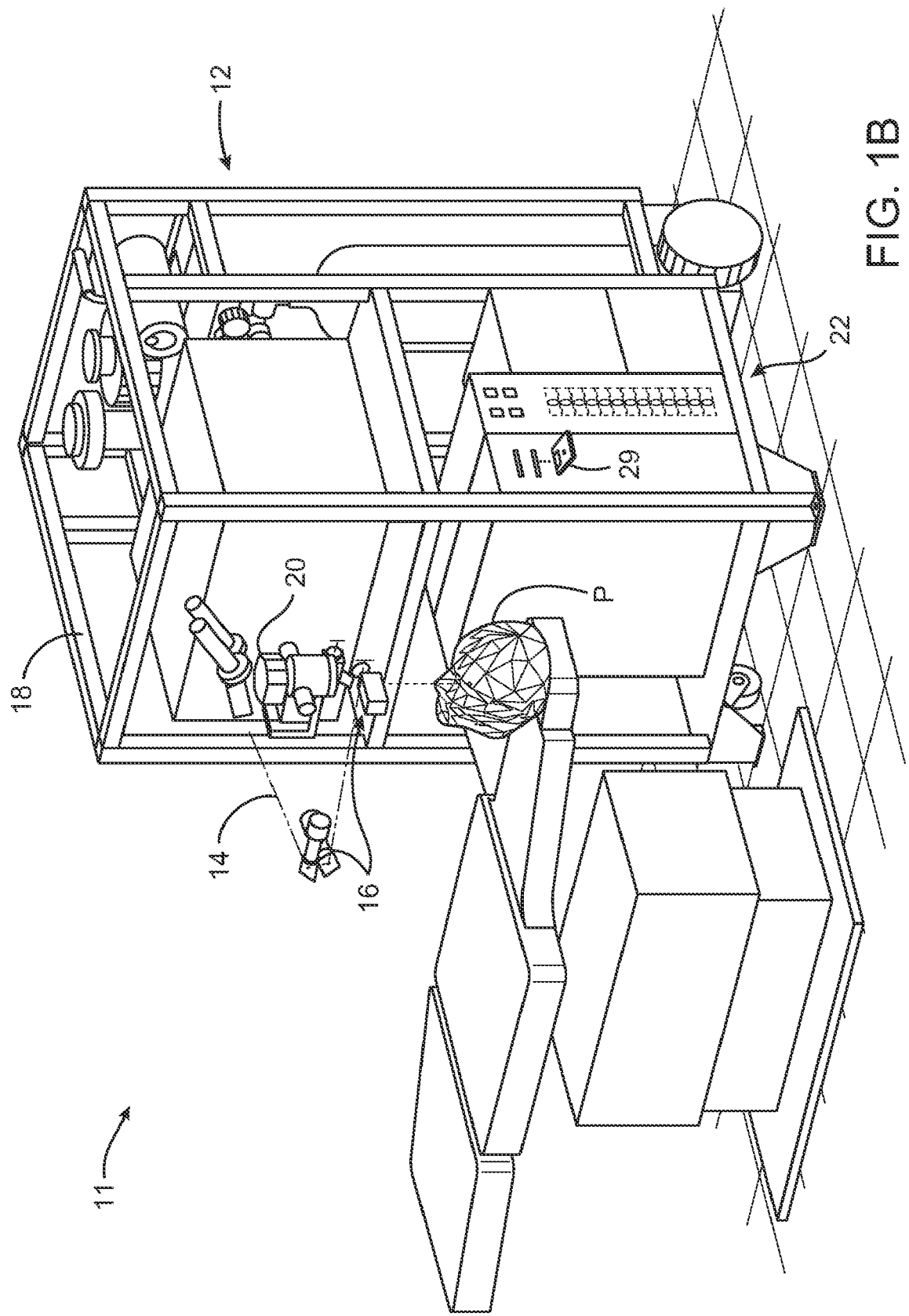

NON-INVASIVE MEASUREMENT OF TEAR VOLUME SYSTEMS AND METHODS

CROSS REFERENCE TO RELATED APPLICATION DATA

The present application is a continuation of U.S. Ser. No. 11/335,861 filed Jan. 18, 2006; the full disclosure of which is incorporated herein by reference in its entirety.

BACKGROUND OF THE INVENTION

The present invention is generally related to measurements of eyes and systems for measuring ocular surfaces. The invention provides devices, systems, and methods for measurement of hydration and tear volume of an eye in conjunction with measurements of optical errors of the eye and refractive properties of the surfaces of the eye, and is particularly well-suited for diagnosing conditions of the eye in relation to physiologic conditions and refractive properties of the eye. The invention is also particularly well suited to the measurement of eyes in conjunction with diagnosis and correction of optical errors of the eye, including correction with optical surfaces such as lenses, spectacles and contacts.

Known laser eye surgery procedures generally employ an ultraviolet or infrared laser to remove a microscopic layer of stromal tissue from the cornea of the eye. The laser typically removes a selected shape of the corneal tissue, often to correct refractive errors of the eye. Ultraviolet laser ablation results in photodecomposition of the corneal tissue, but generally does not cause significant thermal damage to adjacent and underlying tissues of the eye. The irradiated molecules are broken into smaller volatile fragments photochemically, directly breaking the intermolecular bonds.

Laser ablation procedures can remove the targeted stroma of the cornea to change the cornea's contour for varying purposes, such as for correcting myopia, hyperopia, astigmatism, and the like. Control over the distribution of ablation energy across the cornea may be provided by a variety of systems and methods, including the use of ablatable masks, fixed and moveable apertures, controlled scanning systems, eye movement tracking mechanisms, and the like. In known systems, the laser beam often comprises a series of discrete pulses of laser light energy, with the total shape and amount of tissue removed being determined by the shape, size, location, and/or number of laser energy pulses impinging on the cornea. A variety of algorithms may be used to calculate the pattern of laser pulses used to reshape the cornea so as to correct a refractive error of the eye. Known systems make use of a variety of forms of lasers and/or laser energy to effect the correction, including infrared lasers, ultraviolet lasers, femtosecond lasers, wavelength multiplied solid-state lasers, and the like. Alternative vision correction techniques make use of radial incisions in the cornea, intraocular lenses, removable corneal support structures, and the like.

Known corneal correction treatment methods have generally been successful in correcting standard vision errors, such as myopia, hyperopia, astigmatism, and the like. However, as with all successes, still further improvements would be desirable. Toward that end, wavefront measurement systems are now available to measure the refractive characteristics of a particular patient's eye. By customizing an ablation pattern based on wavefront measurements and providing improved laser system calibration, it may be possible to correct minor refractive errors so as to reliably and repeatably provide visual acuities greater than 20/20.

Known methods for calculation of a customized ablation pattern using wavefront sensor data generally involves mathematically modeling an optical surface of the eye such as a measured wavefront elevation map and can include corneal topography of the eye. Such work generally assumes that the refractive properties of the eye and surfaces of the eye are stable. Work in connection with the present invention suggests that the known methodology for measuring eyes in relation to refractive surgery and other correction of refractive errors of the eye may be less than ideal.

In light of the above, it would be desirable to provide improved optical measurement techniques, particularly for use in measurements of the eye for refractive correction purposes.

BRIEF SUMMARY OF THE INVENTION

The present invention generally provides improved devices, systems, and methods for measuring, diagnosing and/or characterizing eyes. Exemplary embodiments provide systems and methods for measuring, diagnosing and characterizing physiologic and optical properties of eyes, such as hydration and tear volume in relation to an optical surface of the eye, such as topography of a corneal surface of the eye and/or a wavefront elevation map of the eye. The system can measure a pupil size of the eye, tear volume, and a wavefront and/or topography of the eye. The system images the eye to form an image of a meniscus formed in a tear rivulet along a margin of an eyelid. The eye can be illuminated so that the meniscus appears as a dark band in the image of the eye. The system can measure tear volume from on the image of the meniscus. For example, tear volume can be determined by measuring a dimension across the tear meniscus, such as the height of the meniscus, as measured from the intersection of the meniscus with the margin of the eyelid to the inward boundary of the meniscus toward the pupil. The regularity of the meniscus height along the eyelid margin can be used to determine whether the tear volume is normal. The tear volume can be used to determine the optical properties of the tear of the eye and to diagnose conditions of the eye such as decreased tear production, decreased tear lipid levels, and irregular cornea resulting from irregular epithelial and/or stromal corneal surfaces. The patient can be screened for correction of the eye with refractive surgery using the measured pupil size, tear volume and topography and/or wavefront.

In a first aspect, the invention provides a method of measuring an eye of a patient. The eye is positioned at a measurement location. The tear volume is determined at the measurement location by measuring a meniscus of a tear fluid on the eye. A topography and/or a wavefront of the eye is measured at the eye measurement location. The meniscus of the eye can be measured by forming an image of the eye with an optical train. The measured meniscus can be disposed along a lid of the eye and within the image. The topography or wavefront of the eye can be diagnosed with the image of the eye. A refractive prescription derived from the topography or wavefront can be registered with the eye using the image. The topography or wavefront of the eye can be measured using at least a portion of the optical train. The image of the eye can be formed by illuminating the eye to form a dark band in the image in which the dark band corresponds to the meniscus. A dimension across the meniscus of the tear of the eye can be measured. The lid of the eye can comprise a margin, and the dimension across the meniscus can correspond to a meniscus height from the margin of the lid of the eye to an inward edge of the meniscus. A regularity of the meniscus along the eyelid can be measured. A volume of the fluid on the eye can be measured. The tear volume can be measured without touching the eye with a foreign object. A size of a pupil formed in an iris of the eye can be determined while the eye is at the measurement location. The eye can be screened for refractive surgery using the tear volume and the size of the pupil. The patient can be warned of delayed recovery in response to the determined tear volume. The patient can be screened for refractive surgery with measurements as described above, and the patient can be monitored with measurements as described above. A condition of the eye can be diagnosed, such as an irregular cornea, pyterigium, tear deficiency or lipid abnormality. A user can generate a signal from an operator control, and the system can respond to the signal by determining the tear volume and measuring the topography or the wavefront.

In another aspect, the invention comprises a system for evaluating an eye of a patient. A first detector captures wavefront or topography measurements from the eye when the eye is at an eye measurement location. A second detector captures an image of the eye when the eye is at the eye measurement location. The image comprises a tear fluid meniscus along a lid of the eye. A processor is coupled to the first and second detectors. The processor determines the optical characteristics of the eye and measures tear volume in response to the tear fluid meniscus. An optical train can form the image of the eye, and the meniscus can be within the image and disposed along a lid of the eye. The processor can diagnose the topography or wavefront of the eye with the image of the eye. The processor can register a refractive prescription derived from the topography or wavefront with the eye using the image. A portion of the optical train can be disposed between the eye and the first detector to capture the wavefront or topography measurements. The tear volume can correspond to a dimension across the meniscus of the tear. A first group of pixels of a sensor array can include the first detector and a second group of pixels of the sensor array can include the second detector. The processor can determine a size of a pupil formed in an iris of the eye. A lenslet array can pass light energy to the first detector, the first detector can include a first array detector. A lens can pass light energy to the second detector, and the second detector can include a second array detector. The processor can determine a wavefront elevation map from the light energy measured with the first array detector and determine a dimension across the meniscus from the image captured with the second array detector. The first detector can capture the wavefront or topography measurement in response to a user generated signal, and the second detector can capture the image of the eye in response to the user generated signal. The first detector can capture the wavefront or topography measurement within one second of the second detector capturing the image of the eye. The processor can diagnose a condition of the eye comprising an irregular cornea, pyterigium, tear deficiency or lipid abnormality. The processor can generate a signal in response to tear volume below a threshold amount.

In another aspect, the invention can comprise a computer-readable storage medium which includes a set of instructions for a computer to diagnose an eye with a tear volume and a wavefront or topography of the eye. An input routine is operatively associated with a first source of wavefront or topography data and a second source of tear volume data. A run routine diagnoses the eye with the wavefront or topography data and the tear volume data. An output routine provides the diagnosis of the eye available for external use outside the computer.

In a further aspect, the invention provides a system for evaluating an eye of a patient. A first detector captures wavefront or topography measurements from the eye when the eye is at an eye measurement location. A second detector captures an image of the eye when the eye is at the eye measurement location, and the image includes a tear fluid meniscus along a lid of the eye. A processor is coupled to the first and second detectors, and the processor determines optical characteristics of the eye and measures hydration of the eye in response to the tear fluid meniscus.

BRIEF DESCRIPTION OF THE DRAWINGS

FIG. 1B illustrates a laser ablation system which can be used with the eye measurement system.

DETAILED DESCRIPTION OF THE INVENTION

Figure 1:
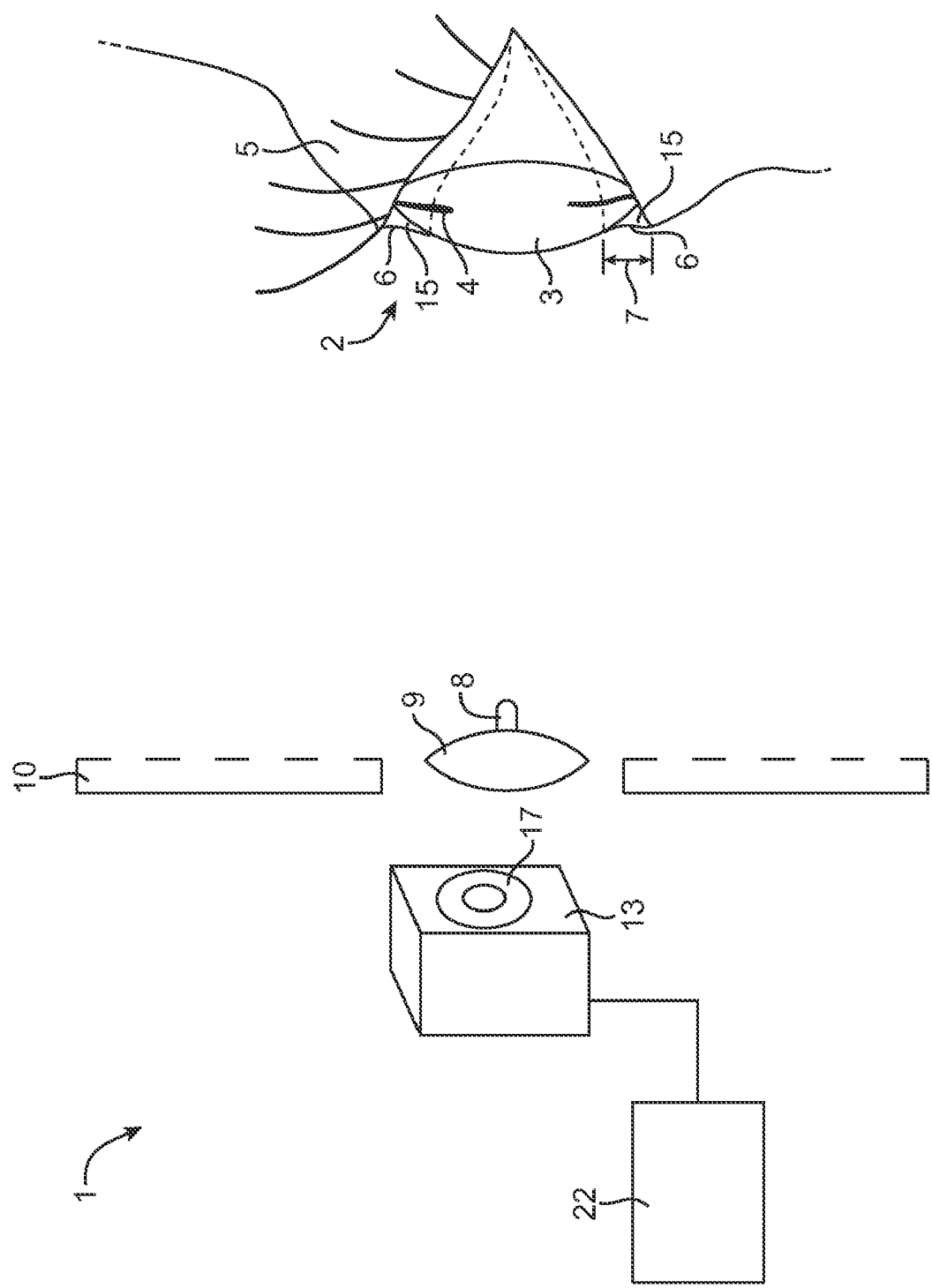
FIG. 1 illustrates an eye measurement system capable of measuring tear volume of an eye and a wavefront and a topography of the eye.

The present invention may be particularly useful for enhancing the accuracy and efficacy of laser eye surgical procedures, such as photorefractive keratectomy (PRK), photo-therapeutic keratectomy (PTK), laser in situ keratomileusis (LASIK), radial keratotomy (RK) and the like. Enhanced optical accuracy of refractive procedures may be provided by improving the methodology for measuring, determining and deriving a corneal ablation or other refractive treatment program. The techniques described herein can be readily adapted for use with existing laser systems, wavefront sensors, and other optical measurement devices. By providing a more direct (and hence, less prone to noise and other error) methodology for measuring and correcting errors of an optical system, these techniques may facilitate sculpting of the cornea so that treated eyes regularly exceed the normal 20/20 threshold of desired vision. While these systems, software, and methods are described primarily in the context of a laser eye surgery system, alternative eye treatment procedures and systems such as spectacle lenses, intraocular lenses, contact lenses, corneal ring implants, collagenous corneal tissue thermal remodeling, and the like may also be employed. The hydration of the eye can be measured with systems and methods similar to those described herein to measure the tear volume.

Systems which can be used to measure the optical aberrations of the eye are numerous and include the phoropter, corneal topography machines, auto refractors and wavefront sensors. The phoropter has several lenses which can be selected and placed in front of a patient to correct a patients vision, often in conjunction with subjective visual testing in which the patient provides feedback as to the clarity of visual stimuli. Corneal topography machines measure the front surface, or topography, of the front surface of cornea of the eye. Wavefront sensors will typically measure aberrations and other optical characteristics of an entire optical system. The data from such a wavefront sensor may be used to generate an optical surface from an array of optical gradients. The optical surface need not precisely match an actual tissue surface, as the gradients will show the effects of aberrations which are actually located throughout the ocular tissue system. Nonetheless, corrections imposed on an optical tissue surface so as to correct the aberrations derived from the gradients or other information should correct the optical tissue system. As used herein the terms such as "an optical tissue surface" may encompass a theoretical tissue surface (derived, for example, from wavefront sensor data), an actual tissue surface (derived, for example, from corneal topography), and/or a tissue surface formed for purposes of treatment (for example, by incising corneal tissues so as to allow a flap of the corneal epithelium to be displaced and expose the underlying stroma during a LASIK procedure).

The interface between air and the liquid tear film covering the cornea provides the greatest refractive power of any surface of the eye. To this end, measurements of the optical properties of the eye in conjunction with measurements of the tear volume and integrity of the tear film of the eye can be beneficial and help with corrective diagnosis and procedures. In a normal healthy eye, the liquid tear film is abundant and covers the front surface of the cornea to provide an optically smooth surface at the front of the eye. In the healthy eye, evaporation of the tear film is decreased by a lipid layer at the surface of the tear film. As the integrity of the lipid layer deteriorates, evaporation of the tear film can increase. Thus, the integrity of the lipid layer at the anterior surface of the eye can affect tear volume, and evaluation of the tear volume can be helpful in determining the optical properties of the eye.

It can be desirable to determine to what extent the tear film of the eye contributes to the optical properties of the eye in comparison to the optical contribution of the underlying corneal epithelial and stromal surfaces. The tear film of the human eye generally includes a lipid layer, an aqueous layer and a mucous layer. Eyes which do not have sufficient aqueous and mucous production or lack sufficient tear lipid content can display a rough or irregular corneal surface, even in cases where the underlying corneal epithelial and stromal layers are smooth.

In general, techniques for determining an optical correction of the eye can assume that the aberrations of the eye are static, and can be fixed with a static and ideally permanent solution. As the tear film presents a dynamic ocular surface which can change with the blink of an eye, an improved understanding of the tear film in relation to measurements of optical surfaces of the eye can provide improved measurement and correction of optical errors of the eye.

Referring now to FIG. 1, an eye measurement system 1 can measure an eye 2 of a patient. The eye measurement system can include a pupil measurement system, a corneal topography measurement system, and a wavefront measurement in conjunction with a measurement of the tear liquid covering the eye. In exemplary embodiments the measurement of the corneal topography, wavefront, and pupil of the eye are simultaneous with the measurement of the tear liquid covering the eye. The eye has a cornea 3 and an iris 4. An eyelid 5 often partially covers the cornea of the eye. A pupil is formed in the iris of the eye. A tear liquid often covers the front surface of the cornea and forms a rivulet 15 adjacent the eyelid. A meniscus 6 forms in the rivulet. The rivulet can form near the upper eyelid of the patient and also near the lower eyelid of the patient. The meniscus has a height 7. The height of the meniscus can be measured as a distance from a margin of the eyelid adjacent the meniscus to a boundary between the ocular surface and an inward (toward the pupil) edge of the tear rivulet. Tear volume is generally related to the height of the meniscus. The volume of the tear fluid in the eye is related to meniscus height. Approximately seventy percent of tear fluid covering an eye can be present in the upper and lower rivulets. Accordingly, a determination of an amount of tear fluid in each of the tear rivulets can be used to determine a volume of tear fluid covering the eye. The amount of fluid in a tear rivulet can be calculated from the product of a cross sectional area of the tear rivulet and the length of the tear rivulet. This calculation can be done for both the upper and lower tear rivulets. The height of the tear film meniscus is related to the cross sectional area of the tear rivulet. Therefore, a determination of the height of the tear film meniscus can be correlated with the volume of fluid in the tear rivulets and the total volume of tear fluid covering the eye. In clinical practice it is not necessary to determine a total volume of tear fluid covering the eye to diagnose conditions of the eye. The meniscus height corresponds to the cross sectional area of the rivulet and tear volume. Consequently a determination of meniscus height and/or regularity of the meniscus height along the eyelid margin can be sufficient to diagnose a condition of the tear integrity. Diagnosis of the condition of the eye typically encompasses informing the patient of the ocular condition and writing the diagnosed condition of the eye in a patient chart.

In some embodiments, an eye measurement system is a topography system which measures a front surface of the cornea of the eye including the tear liquid covering the eye. As shown in FIG. 1 a placido disc 10 is used to reflect images of concentric rings of light from the front surface of the eye. Although a Placido disc is illustrated in FIG. 1, any topography system can be used in conjunction with the hydration and tear volume measurements herein described. For example, U.S. Pat. No. 6,050,687, entitled "Method and apparatus for measurement of the refractive properties of the human eye", issued to Bille, the full disclosure of which is incorporated herein by reference, describes a corneal topography machine using a lenslet array, in which the topography machine is integrated with a wavefront sensor measuring the refraction of light transmitted through the eye.

Figure 1A:
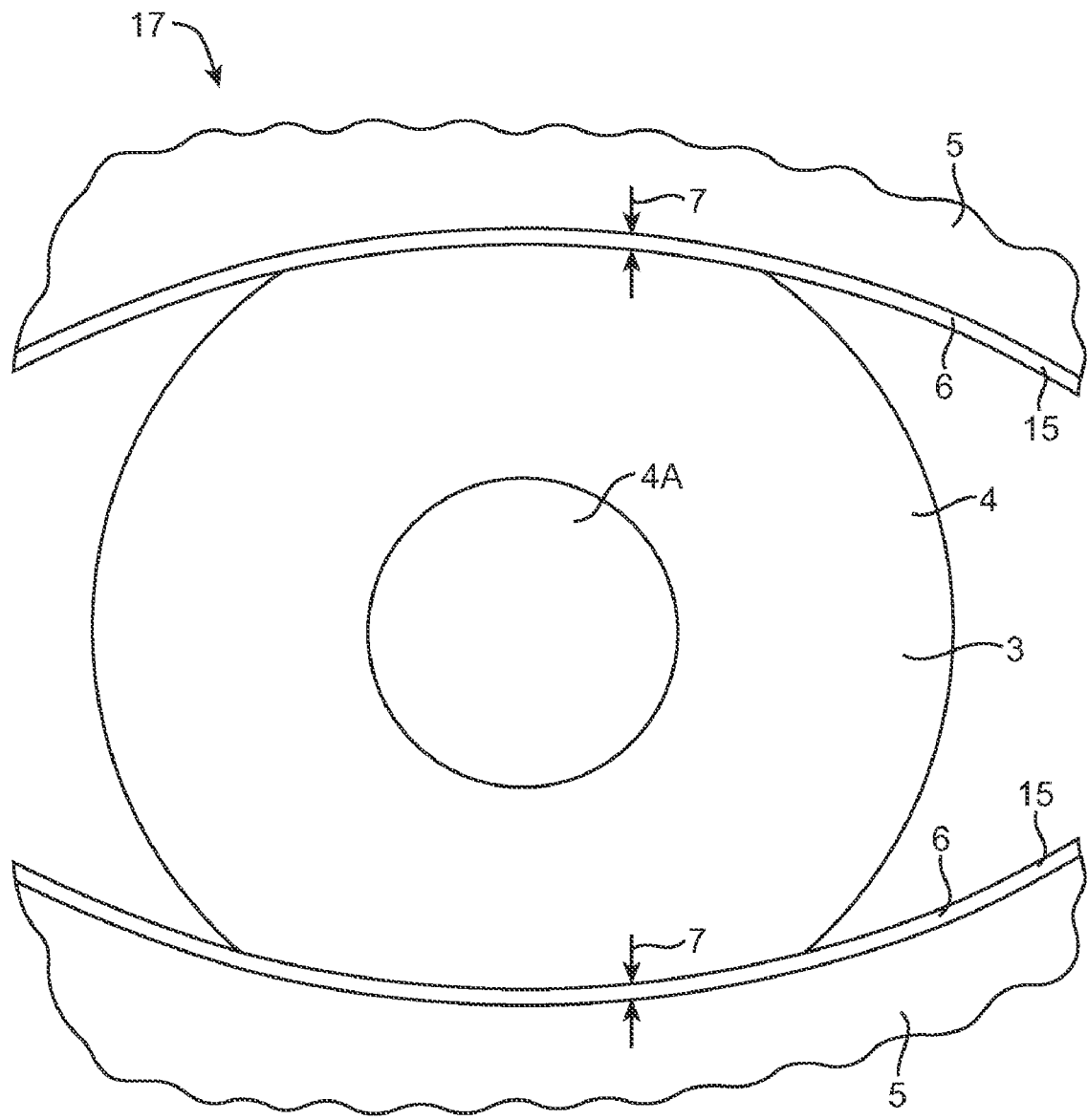
FIG. 1A illustrates an image of an eye having a tear meniscus.

Referring now to FIGS. 1 and 1A, a lens 9 passes light reflected from the cornea of the eye and forms an image 17 on a sensor array 13. A light source 8 such as an LED can be positioned near the lens 9 to project light onto the eye. The projection of light source 8 can be in addition to light from other sources, and light source 8 can be combined with other sources of light. In many embodiments, the light source can be positioned to illuminate the iris of the eye so that the pupil appears as a dark region in the image formed on the sensor array. The light source can also be positioned so that the tear rivulet and meniscus appear as a dark band in the image of the tear film of the eye. In alternate embodiments light is reflected from the tear rivulet and meniscus, and this reflected light appears in the image of the eye. For example, light from the Placido disc can be reflected from the meniscus and appear in the image of the eye so as to permit determination of the height of the meniscus from the distorted image of the Placido disc reflected from the meniscus as seen in the image of the eye. In alternate embodiments, light emitting diodes (LEDs) are arranged to form patterns from light reflected from the tear meniscus which can be analyzed. For example, the journal article "Reflective meniscometry: a non-invasive method to measure tear meniscus curvature" describes patterns of light which can be reflected from the eye to determine the height of the meniscus formed in the tear rivulet. Br. J. Opthalmology 1999; 83; 92-97, http://www.bjo.bmjjournals.com/cgi/content/full/83/1/92.

The sensor array can include an area CCD array, an area CMOS sensor array and a linear sensor array in which pixels of the linear array are disposed along a line. A processor 22 is electronically coupled to the sensor array to determine information about the eye. Information about the eye can include corneal topography information, wavefront information of the entire ocular path of the eye and a diameter of the pupil of the eye. The information determined by the eye measurement system can be used to treat the eye.

Referring now to FIG. 1B, a laser eye surgery system 11 includes a laser 12 that produces a laser beam 14. Laser 12 is optically coupled to laser delivery optics 16, which directs laser beam 14 to an eye of patient P. A delivery optics support structure (not shown here for clarity) extends from a frame 18 supporting laser 12. A microscope 20 is mounted on the delivery optics support structure, the microscope often being used to image a cornea of the eye.

Laser 12 generally comprises an excimer laser, ideally comprising an argon-fluorine laser producing pulses of laser light having a wavelength of approximately 193 nm. Laser 12 will preferably be designed to provide a feedback stabilized fluence at the patient's eye, delivered via laser delivery optics 16. Alternative sources of ultraviolet or infrared radiation may also be used, particularly those adapted to controllably ablate the corneal tissue without causing significant damage to adjacent and/or underlying tissues of the eye. In some embodiments, the laser beam source employs a solid state laser source having a wavelength between 193 and 215 nm as described in U.S. Pat. Nos. 5,520,679 and 5,144,630 to Lin, and 5,742,626 to Mead, the full disclosures of which are incorporated herein by reference. In some embodiments, the laser source includes an infrared laser as described in U.S. Pat. Nos. 5,782,822 and 6,090,102 to Telfair, the full disclosures of which are incorporated herein by reference. Hence, although an excimer laser is the illustrative source of an ablating beam, other lasers may be used.

Laser 12 and laser delivery optics 16 will generally direct laser beam 14 to the eye of patient P under the direction of a computer system 22. Computer system 22 will often selectively adjust laser beam 14 to expose portions of the cornea to the pulses of laser energy so as to effect a predetermined sculpting of the cornea and alter the refractive characteristics of the eye. In many embodiments, both laser 12 and the laser delivery optical system 16 will be under control of computer system 22 to effect the desired laser sculpting process, with the computer system effecting (and optionally modifying) the pattern of laser pulses. The pattern of pulses may be summarized in machine readable data of tangible media 29 in the form of a treatment table, and the treatment table may be adjusted according to feedback input into computer system 22 from an automated image analysis system (or manually input into the processor by a system operator) in response to real-time feedback data provided from an ablation monitoring feedback system. The laser treatment system, and computer system 22 may continue and/or terminate a sculpting treatment in response to the feedback, and may optionally also modify the planned sculpting based at least in part on the feedback.

Additional components and subsystems may be included with laser system 11, as should be understood by those of skill in the art. For example, spatial and/or temporal integrators may be included to control the distribution of energy within the laser beam, as described in U.S. Pat. No. 5,646,791, the full disclosure of which is incorporated herein by reference. Ablation effluent evacuators/filters, aspirators, and other ancillary components of the laser surgery system are known in the art. Further details of suitable systems for performing a laser ablation procedure can be found in commonly assigned U.S. Pat. Nos. 4,665,913; 4,669,466; 4,732,148; 4,770,172; 4,773,414; 5,207,668; 5,108,388; 5,219,343; 5,646,791; and 5,163,934, the complete disclosures of which are incorporated herein by reference. Suitable systems also include commercially available refractive laser systems such as those manufactured and/or sold by Alcon, Bausch & Lomb, Nidek, WaveLight, LaserSight, Schwind, Zeiss Meditec, and the like.

Figure 2:
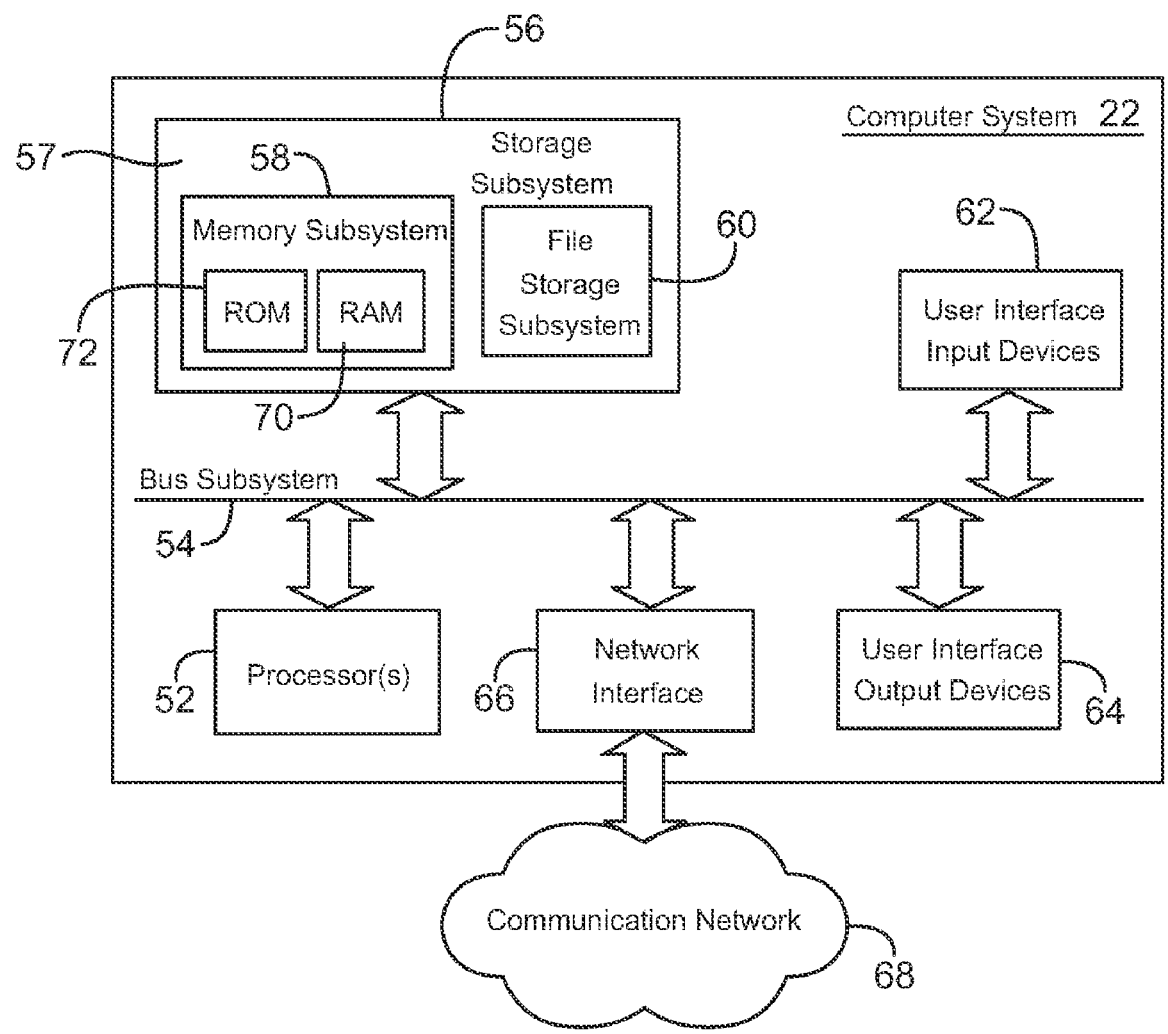
FIG. 2 illustrates a simplified computer system which can be used with the laser ablation system and/or the eye measurement system.

FIG. 2 is a simplified block diagram of an exemplary computer system 22 that may be used by laser surgical system 11. Computer system 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices, such as the wavefront measurement system 30.

User interface input devices 62 may include a keyboard, pointing devices such as a mouse, trackball, touch pad, or graphics tablet, a scanner, foot pedals, a joystick, a touchscreen incorporated into a display 28, audio input devices such as voice recognition systems, microphones, and other types of input devices. User input devices 62 will often be used to download a computer executable code from a tangible storage media 29 embodying any of the methods described herein.

User interface output devices 64 may include display 28, a printer, a fax machine, or non-visual displays such as audio output devices. The display may be a cathode ray tube (CRT), a flat-panel device such as a liquid crystal display (LCD), a projection device, or the like. The display may also provide a non-visual display such as via audio output devices.

Storage subsystem 56 stores the basic programming and data constructs that provide the functionality of the various embodiments of the methods described herein. For example, a database and modules implementing the functionality of the methods, as described herein, may be stored in storage subsystem 56. These software modules generally are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of program instructions and data during program execution and a read only memory (ROM) 72 in which fixed instructions are stored. File storage subsystem 60 provides persistent (non-volatile) storage for program and data files, and may include tangible storage media 29 (FIG. 1) which may optionally embody wavefront sensor data, wavefront gradients, a wavefront elevation map, a treatment map, and/or an ablation table. File storage subsystem 60 may include a hard disk drive, a floppy disk drive along with associated removable media, a Compact Digital Read Only Memory (CD-ROM) drive, an optical drive, DVD, CD-R, CD-RW, solid-state removable memory, and/or other removable media cartridges or disks including flash RAM. One or more of the drives may be located at remote locations on other connected computers at other sites coupled to computer system 22. The modules implementing the functionality of the techniques described herein may be stored by file storage subsystem 60. Storage sub system 56 can include any computer readable storage medium 57. For example, computer readable storage medium 57 can include any computer readable storage medium described in the memory subsystem and any computer readable storage medium described in the file storage system. For example, computer readable storage medium 57 can include temporary storage in the random access memory.

Bus subsystem 54 provides a mechanism for letting the various components and subsystems of computer system 22 communicate with each other as intended. The various subsystems and components of computer system 22 need not be at the same physical location but may be distributed at various locations within a distributed network. Although bus subsystem 54 is shown schematically as a single bus, alternate embodiments of the bus subsystem may utilize multiple busses.

Computer system 22 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of computer system 22 depicted in FIG. 2 is intended only as a specific example illustrating one embodiment. Many other configurations of computer system 22 are possible having more or less components than the computer system depicted in FIG. 2.

Figure 3:
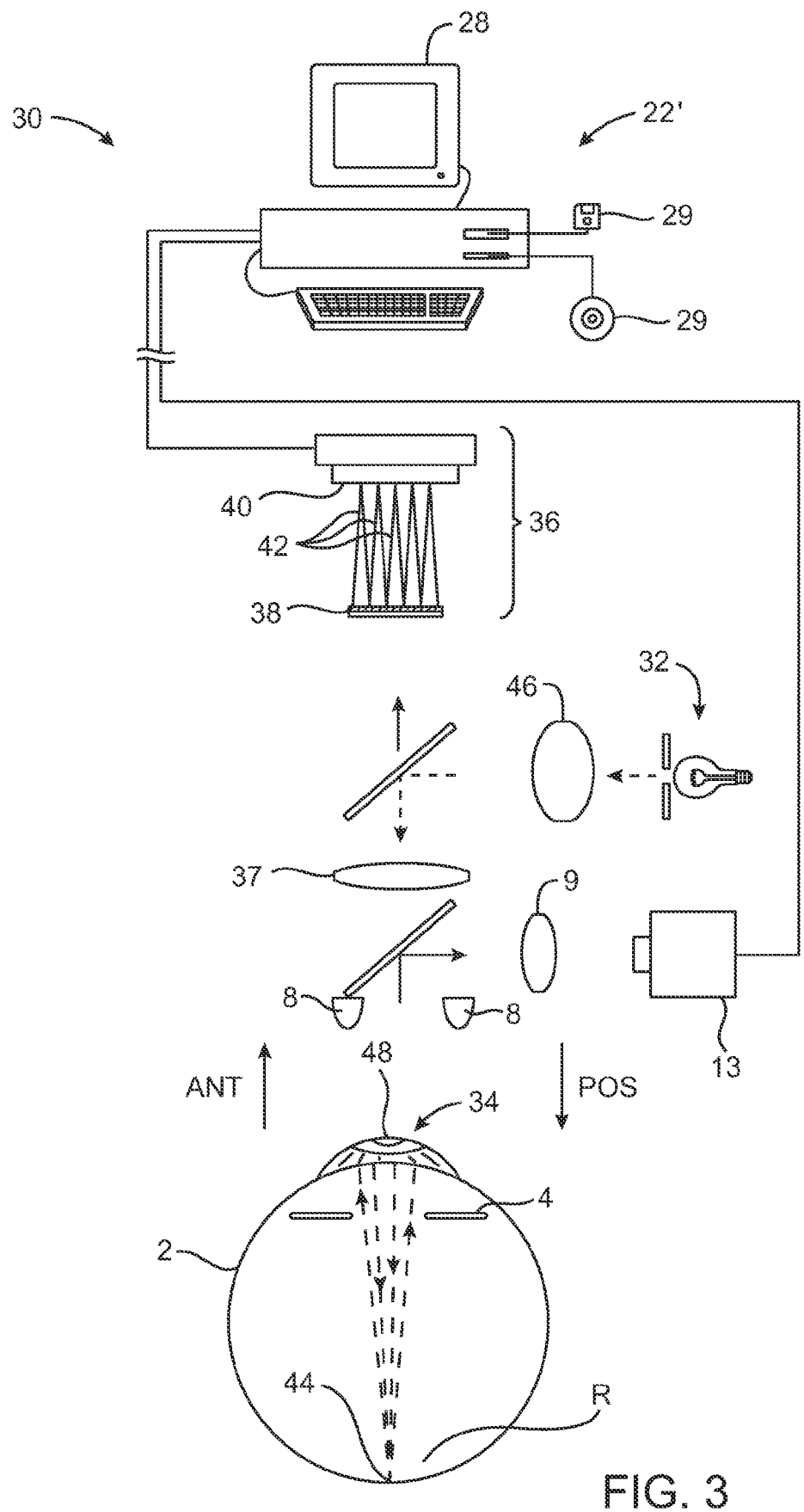
FIG. 3 illustrates a wavefront measurement system capable of measuring eyes.

Referring now to FIG. 3, one embodiment of a wavefront measurement system 30 is schematically illustrated in simplified form. In very general terms, wavefront measurement system 30 is configured to sense local slopes of a gradient map exiting the patient's eye. Wavefront system 30 generally can include a lenslet array to sample the gradient map uniformly over an aperture, which is typically the exit pupil of the eye. Thereafter, the local slopes of the gradient map can be analyzed so as to reconstruct the wavefront surface or map.

More specifically, wavefront measurement system 30 can include an image source 32, such as a laser, which projects a source image through optical tissues 34 of eye 2 so as to form an image 44 upon a surface of retina R. Image 44 can comprise a very tiny spot of light and can be formed by imaging light passing through an aperture positioned near source 32. The image from retina R is transmitted by the optical system of the eye (e.g., optical tissues 34) and imaged onto a wavefront sensor 36 by system optics 37. The wavefront sensor 36 communicates signals to a computer system 22' for measurement of the optical errors in the optical tissues 34 and/or determination of an optical tissue ablation treatment program. Computer 22' may include tangible media embodying instructions or code for characterizing a surface, and/or for the other methods described herein. For example, instructions to diagnose the eye by measuring a wavefront and/or topography and by measuring a tear meniscus. Computer 22' may include the same or similar hardware as the computer system 22 illustrated in FIGS. 1 and 2. Computer system 22' may be in communication with computer system 22 that directs the laser surgery system 11. If desired, data from wavefront sensor 36 may be transmitted to a laser computer system 22 via tangible media 29, via an I/O port, via an networking connection 66 such as an intranet or the Internet, a local area network (LAN) or the like.

Wavefront sensor 36 generally includes a lenslet array 38 and a sensor array such as an image sensor 40. As the image from retina R is transmitted through optical tissues 34 and imaged onto a surface of image sensor 40 and an image of the eye pupil is similarly imaged onto a surface of lenslet array 38, the lenslet array separates the transmitted image into an array of beamlets 42, and (in combination with other optical components of the system) images the separated beamlets on the surface of sensor 40. Sensor 40 can be a charged couple device or "CCD," and senses the characteristics of these individual beamlets, which can be used to determine the characteristics of an associated region of optical tissues 34. In particular, where image 44 comprises a point or small spot of light, a location of the transmitted spot as imaged by a beamlet can directly indicate a local gradient of the associated region of optical tissue. In alternate embodiments, the sensor can be a CMOS sensor array, a linear array detector, orthogonal linear array detectors, a position sensing detector or a quadrant detector.

Eye 2 generally defines an anterior orientation ANT and a posterior orientation POS. Image source 32 generally projects an image in a posterior orientation through optical tissues 34 onto retina R as indicated in FIG. 3. Optical tissues 34 again transmit image 44 from the retina anteriorly toward wavefront sensor 36. As image 44 is actually formed on retina R, image 44 may be distorted by any imperfections in the eye's optical system. Optionally, image source projection optics 46 may be configured or adapted to decrease any distortion of image 44.

In some embodiments, image source optics 46 may decrease lower order optical errors by compensating for spherical and/or cylindrical errors of optical tissues 34. Higher order optical errors of the optical tissues may also be compensated through the use of an adaptive optics system, such as a deformable mirror (described below). Use of an image source 32 selected to define a point or small spot at image 44 upon retina R may facilitate the analysis of the data provided by wavefront sensor 36. Distortion of image 44 may be limited by transmitting a source image through a central region 48 of optical tissues 34 which is smaller than the pupil formed in the iris, as the central portion of the pupil may be less prone to optical errors than the peripheral portion. Regardless of the particular image source structure, it will be generally be beneficial to have a well-defined and accurately formed image 44 on retina R.

The wavefront data may be stored in a computer readable medium 29 or a memory of the wavefront sensor system 30 in three separate arrays containing 1) the light spot pattern, 2) the x and y wavefront gradient values obtained from image spot analysis of the Hartmann-Shack sensor images, and 3) the x and y pupil center offsets from the nominal center of the Hartmann-Shack lenslet array, as measured by the sensor array 13 (FIG. 3) image. Such information can contain information on the wavefront error from one or more wavefront measurements of the eye and be sufficient to reconstruct the wavefront or any portion of it. In other embodiments, the wavefront data may be stored in a memory of the wavefront sensor system in a single array or multiple arrays. In many embodiments additional patient data can be stored such as manifest patient refraction, subjective patient needs and preferences, and data measured with other instruments. While the computer readable medium or memory is shown with respect to the wavefront sensor system, additional memory and computers can be used. For example, computers can share the wavefront information over the local area network (LAN), and the intranet, and the Internet.

While methods will generally be described herein with reference to sensing of an image 44, a series of wavefront sensor data readings may be taken. For example, a time series of wavefront data readings may help to provide a more accurate overall determination of the ocular tissue aberrations. As the ocular tissues can vary in shape over a brief period of time, a plurality of temporally separated wavefront sensor measurements can avoid relying on a single snapshot of the optical characteristics as the basis for a refractive correcting procedure. Still further alternatives are also available, including taking wavefront sensor data of the eye with the eye in differing configurations, positions, and/or orientations. For example, a patient will often help maintain alignment of the eye with wavefront measurement system 30 by focusing on a fixation target, as described in U.S. Pat. No. 6,004,313, the full disclosure of which is incorporated herein by reference. By varying a position of the fixation target as described in that reference, optical characteristics of the eye may be determined while the eye accommodates or adapts to image a field of view at a varying distance and/or angles.

The location of the optical axis of the eye may be verified by reference to the data provided from a sensor array 13. In an exemplary embodiment, lens 9 forms an image of the pupil formed in the iris 4 so as to determine a position of the pupil for registration of the wavefront sensor data relative to the optical tissues.

In an exemplary embodiment illustrated in FIG. 3, each individual light source 8 comprises a pair of light sources which project light onto eye 2. The pair of light sources can be positioned near the lens 9 so that light projected by the light sources illuminates eye 2. Light sources positioned near imaging lens 9 can often produce images having a dark band near the eyelid margin in which the tear meniscus appears as a dark band near the eyelid. Wavelengths from light source 8 can be selected, for example infrared wavelengths, so that the iris appears light even for highly pigmented eyes. A lighter iris shown in the image can be desirable and provide increased contrast between a dark band corresponding to the meniscus and surrounding tissues shown in the image.

Figure 4:
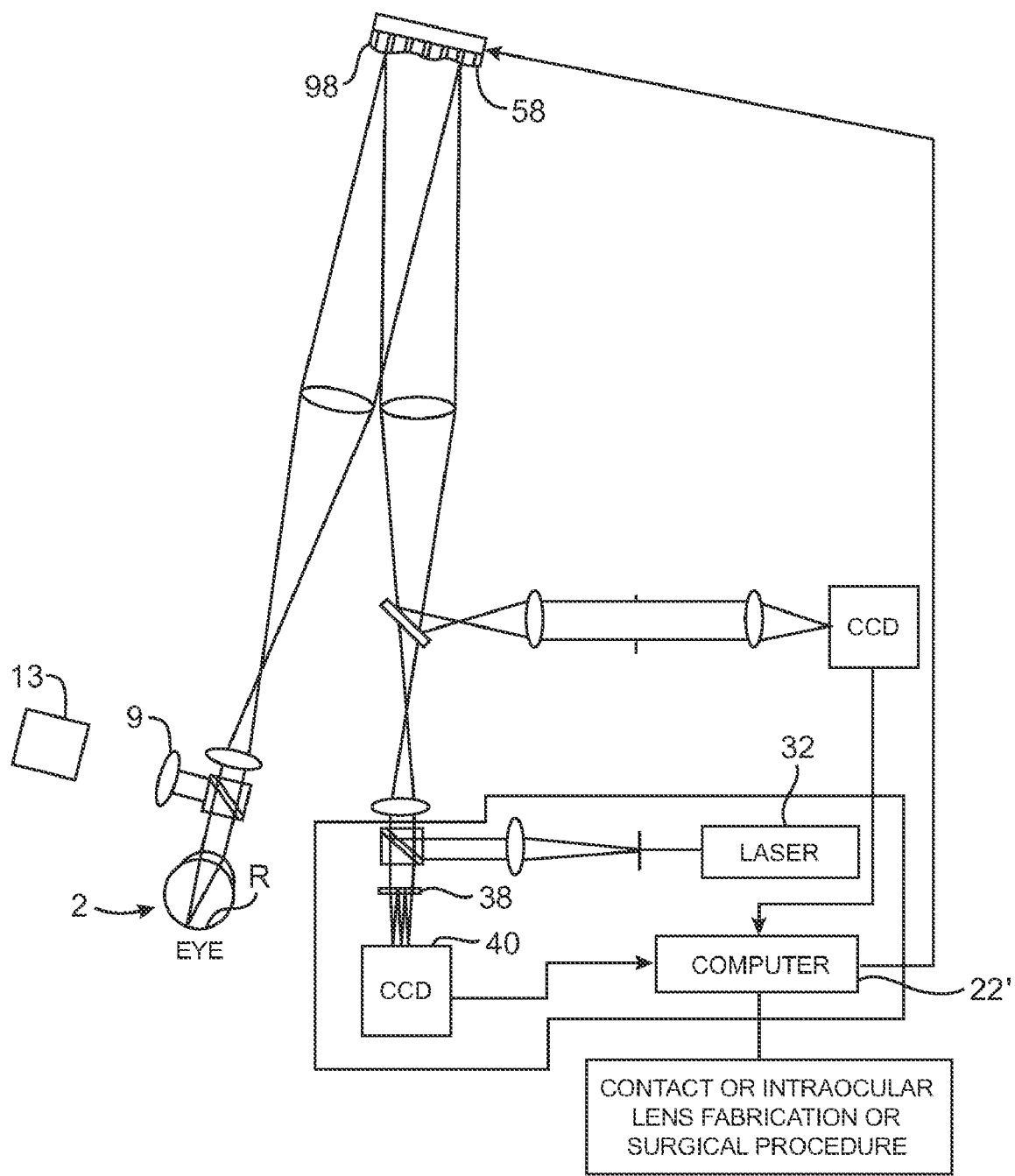
FIG. 4 illustrates another wavefront measurement system capable of measuring eyes and incorporating an adaptive optic.

An alternative embodiment of a wavefront measurement system is illustrated in FIG. 4. The major components of the system of FIG. 4 are similar to those of FIG. 3. Additionally, FIG. 4 includes an adaptive optics system 53 in the form of a deformable mirror 58. The source image is reflected from deformable mirror 58 during transmission to retina R, and the deformable mirror is also along the optical path used to form the transmitted image between retina R and imaging sensor 40. Deformable mirror 58 can be controllably deformed by computer system 22 to limit distortion of the image formed on the retina or of subsequent images formed of the images formed on the retina, and may enhance the accuracy of the resultant wavefront data. The structure and use of the system of FIG. 4 are more fully described in U.S. Pat. No. 6,095,651, the full disclosure of which is incorporated herein by reference.

Figure 5:
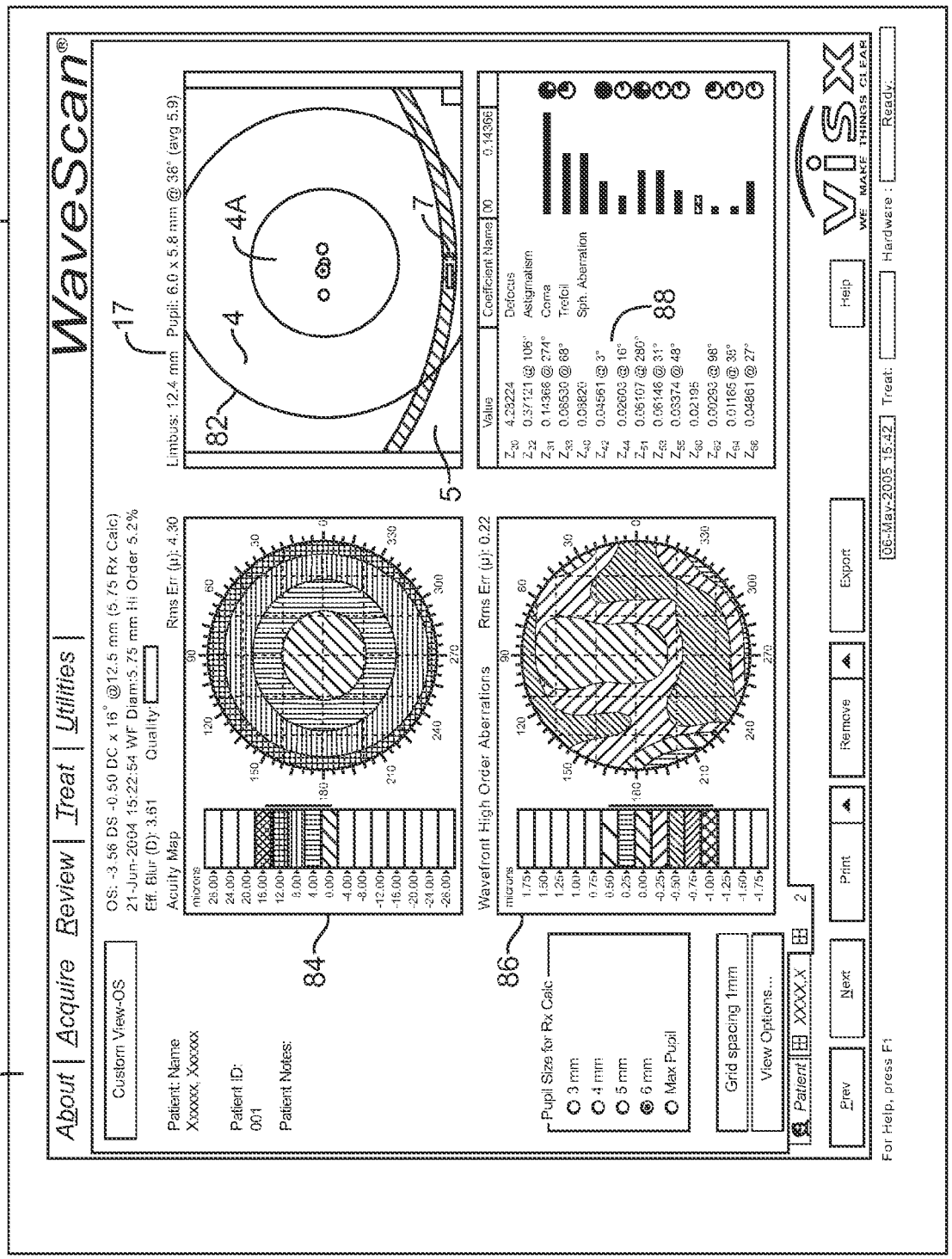
FIG. 5 illustrates output from several eye measurements shown on a display and visible to a user.

Referring now to FIG. 5, output information from several eye measurements are shown on a display. The wavefront of the eye, the pupil of the eye and the tear volume can measured while the eye is positioned at a single measurement location as set forth above. The output device such as display 28 has generated output information 80 visible to a user. The output information includes the image 17, a wavefront elevation map 84, or Acuity Map, a Wavefront High Order Aberration Map 86, and Zernike coefficients 88. In alternate embodiments, spatial frequency components of a Fourier Series can be shown. Maps 82 and 84 show wavefront error in microns over the pupil of the eye. A boundary of a limbus 82 can be shown in image 17, and a boundary of pupil 4A formed in iris 4 of the eye can also be shown in the image. A tear meniscus height 7 can also be shown. In a preferred embodiment, an outer boundary around the dark band corresponding to the tear meniscus formed in the tear rivulet along the margin of the eyelid can be shown in the output information, and an inner boundary of the meniscus formed in the tear rivulet disposed toward the pupil of the eye can be shown in the output information. The tear meniscus height can be measured at several locations along the margin of the eyelid to determine the regularity of the tear meniscus height. A regular tear meniscus has height which varies gradually along the eyelid margin. An irregular tear meniscus has a height which varies rapidly along the eyelid margin and the irregular tear meniscus can indicate dry eye.

The components of an embodiment of a wavefront measurement system for measuring the eye and ablations can include elements of a VISX WaveScan® system, available from VISX, Incorporated of Santa Clara, Calif. One embodiment includes a WaveScan® system with a deformable mirror as described above. An alternate embodiment of a wavefront measuring system is described in U.S. Pat. No. 6,271,915, the full disclosure of which is incorporated herein by reference.

Figure 6A:
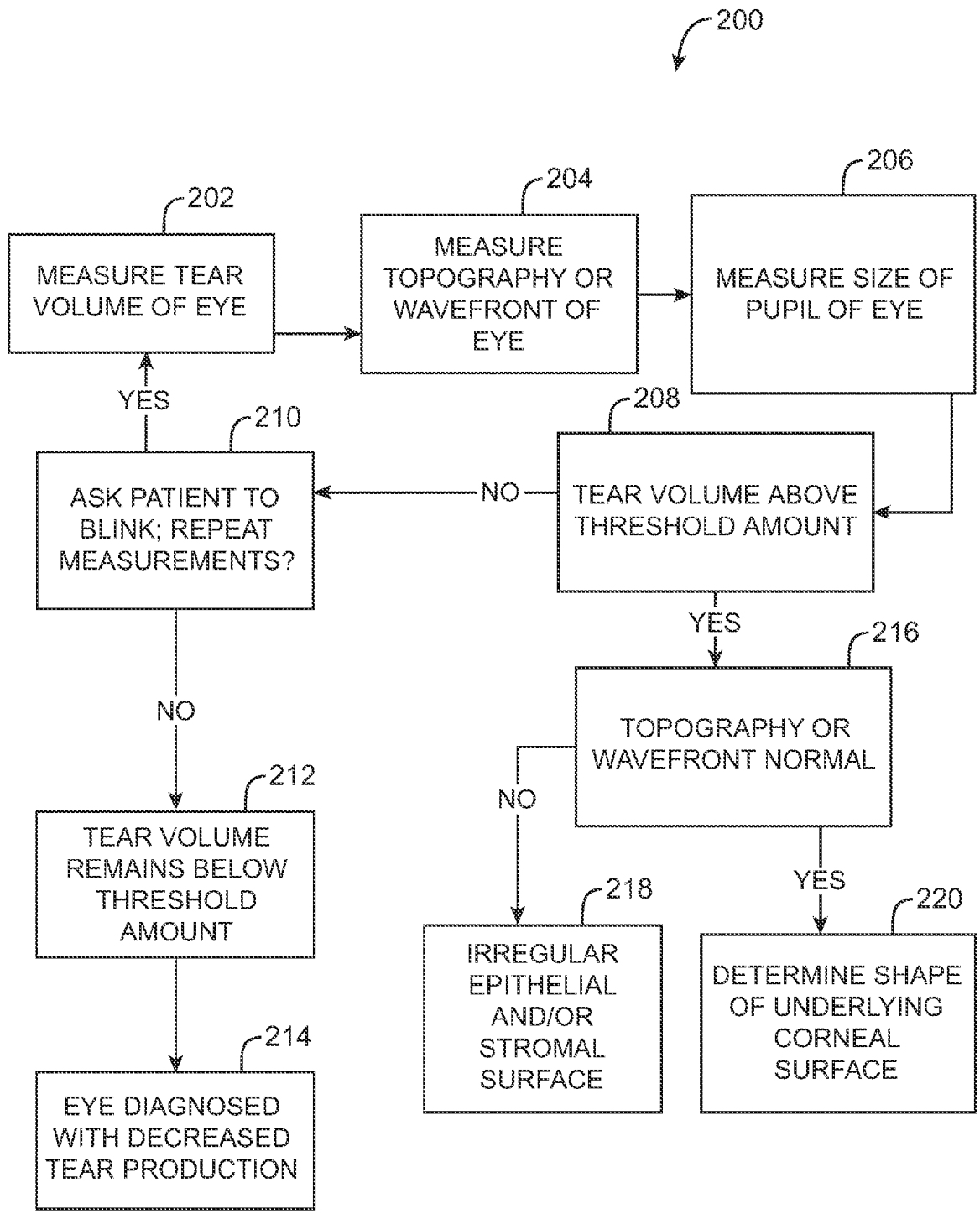
FIG. 6A illustrates methods of measuring a tear volume, a pupil size of an eye and a topography and/or wavefront of the eye.

Referring now to FIG. 6A, techniques of measuring an eye 200 are illustrated, which can be combined with any of the ocular measurement systems described above. These techniques can be implemented with the processor shown above, and can be implemented as machine readable code embedded in a tangible media as described herein. The eye is positioned at the measurement location. The tear volume is measured at step 202. The topography of the eye is measured at step 204. The size of the pupil is measured at step 206. Each of steps 202, 204 and 206 can be performed while the eye is at the measurement location. In a preferred embodiment, the steps 202, 204 and 206 are performed simultaneously in response to a user generated signal, for example the sensor arrays used in steps 202, 204 and 206 sample data for overlapping periods of time. In some embodiments, the measurements at steps 202, 204 and 206 are taken within one second of each other, and in additional embodiments are taken within a quarter second of each other. The measured tear volume is compared to a threshold amount at step 208. In a preferred embodiment tear volume is measured by determining the tear meniscus height at several locations along the eyelid margin. If the tear volume is below the threshold amount, and the measurement steps 202, 204 and 206 have not been repeated while the eye is at the measurement location for the current examination, the patient is asked to blink at step 210, and measurement steps 202, 204 and 206 are repeated. However, if the measurement steps 202, 204 and 206 have been repeated while the eye is at the measurement location for the current examination and the patient has already been asked to blink, the tear volume is determined to remain below the threshold amount at step 212. The eye is diagnosed as having a decreased aqueous production at step 214. Diagnosis of a condition often includes informing the patient of the condition and noting the condition in the patient chart. Additional tests can be performed to determine the cause of decreased patient tear volume. Examples of additional tests include a slit lamp exam to check for lacrimal function, a systemic immune disease checkup, evaluation of current medications, and tear protein analysis. If the tear volume is determined to be above a threshold amount at step 208, the topography and/or wavefront is characterized at step 216. The topography and/or wavefront can be characterized as normal or not normal. If the topography and/or wavefront is not normal at step 216, additional measurements can be taken to determine the cause of the abnormal topography and/or wavefront, for example by evaluating the stability of the topography and/or wavefront. The stability of several measurements taken over time can be analyzed similar to the measurements and analysis described in U.S. Patent Application No. 2004/0212781, the full disclosure of which is incorporated herein by reference. If the topography and/or wavefront is unstable, the abnormality can be associated with the tear film, for example an inadequate lipid layer which permits evaporation of the tear film. If the topography and/or wavefront is stable, the eye can be diagnosed as having a cataract, pyterigium, irregular cornea from an irregular epithelial surface and/or an irregular stromal surface at step 218. Normal topography and/or wavefront measurements can be characterized as corresponding to smooth, specular ocular surfaces, including smooth, specular corneal surfaces following LASIK eye surgery. Topography and wavefront surfaces can also be categorized as normal based on the spatial frequency information present in the measured surface. For example, high spatial frequencies correspond to irregular surfaces, and low spatial frequencies correspond to regular surfaces. If the topography and/or wavefront measurement is normal at step 216, an underlying corneal surface shape can be calculated at step 220. For example, a shape of the underlying corneal surface can be reliably calculated from the measured topography and/or wavefront of the eye, once the tear volume is diagnosed to be healthy and within normal limits. The combined measurements can also be used to diagnose the severity of dry eye, follow the progress of dry eye treatment and document the tear integrity.

Figure 6B:
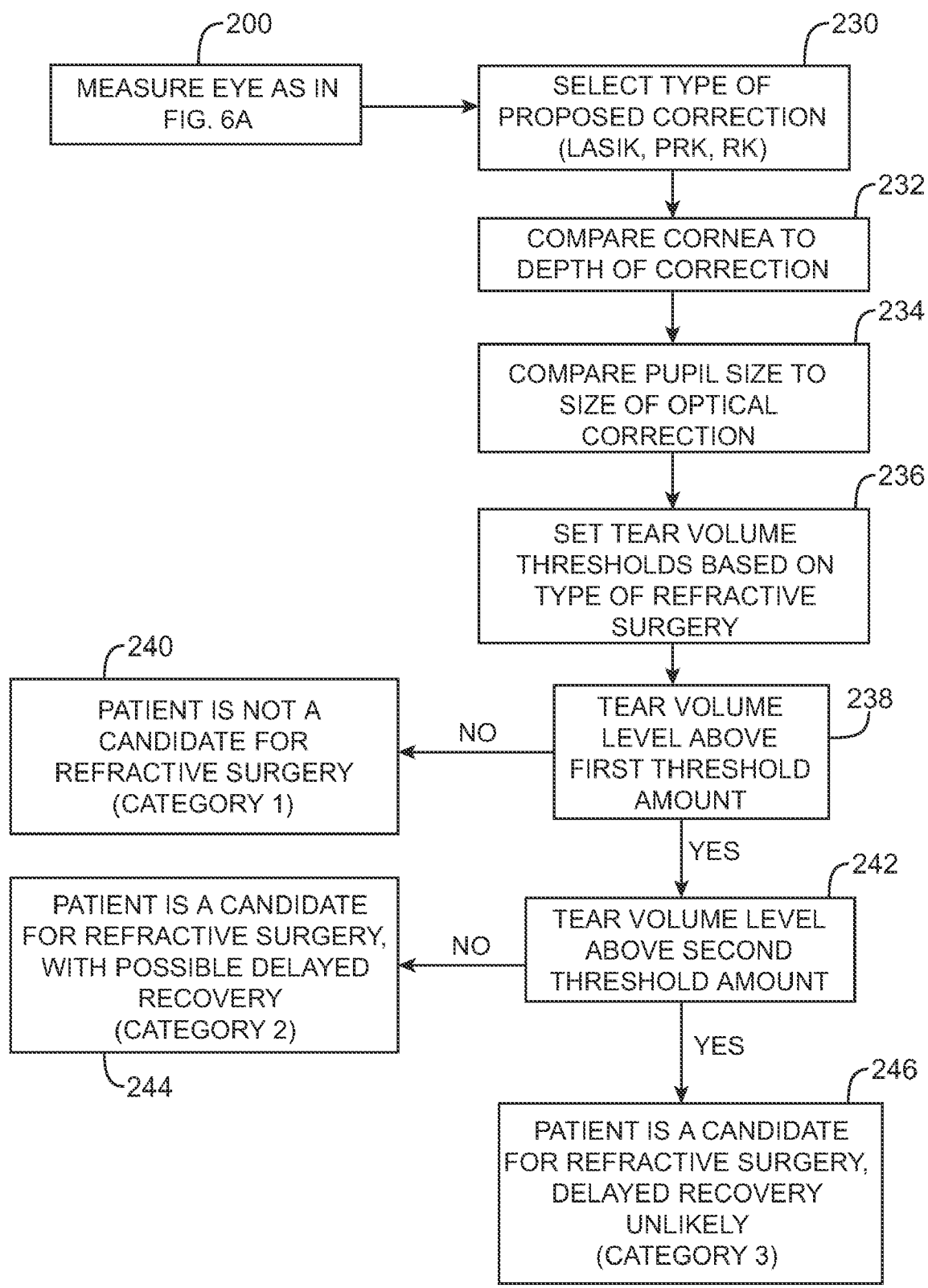
FIG. 6B illustrates techniques for diagnosing conditions of an eye and screening the eye to select a correction for the eye.

FIG. 6B illustrates techniques for diagnosing conditions of an eye and to screen the eye and select a treatment of the eye, such as a refractive surgery, for example LASIK refractive surgery. An eye is measured with techniques 200 as described above. A type of treatment which can be provided to correct optical errors of the eye is selected at step 230. For example, the selected treatment can eyeglasses, contract lenses and surgery such as LASIK, PRK, RK or other corrective eye surgery. A patient can be diagnosed as falling into one of three categories based on comparisons at steps 232, comparison of cornea to depth of correction; step 234, comparison of pupil size to size of optical correction; and steps 236, 238 and 242 comparison of measured tear volume levels to threshold amounts. A first category 240 is the category for which the selected treatment is not indicated. A second category 244 is the category for which the patient is a candidate for the selected treatment and may have a delayed recovery and require additional follow up and guidance. A third category 246 is the category for which the patient is a candidate for selected treatment and is likely to have a rapid recovery with minimal risk of side effects such as delayed recovery of vision, dry eye, and night vision problems. Each of the comparisons at steps 232, 234, 238 and 242 can be used to determine a specific category into which a patient falls with respect to a specific comparison. In general, the overall diagnoses of the condition of a patient for the selected treatment can be determined by comparing the categories determined by comparisons at steps 230 to 246. The overall condition of the patient can be diagnosed as the lowest category among the categories determined by the comparison. For example a patient can be considered to be in category one with respect to comparison of the cornea to depth of treatment at step 232, category two with respect to the comparison of pupil size to the size of the optical treatment at step 234, and category three with respect to tear volume at steps 242 and 246. The overall diagnosis of this patient for the selected treatment is category 1 (240) in which the patient is not a candidate for the selected treatment and the selected treatment is a contraindication.

Several possible combinations of comparisons can be made. For example, the cornea is compared to the depth of the treatment at step 232, and a thickness of stromal bed in LASIK can be compared to the intended depth of ablation. Alternatively, a thickness of a corneal implant, or depth of the implant can be compared to the thickness of the cornea. The size of the treatment is compared to the size of the pupil at step 234. For example, a size of an optical zone ablated on the cornea can be compared to the size of the pupil. Also, a size of an ablation zone including a size of a transition zone can be compared to the size of the pupil. A size of an optical correction zone on a contact lens can be compared to a size of the pupil. An tear volume threshold can be set based on a type of treatment selected for the patient. For example, LASIK, PRK, RK and contact lens fitting can each have different first threshold amounts. The first tear volume threshold can be set at an amount of tear volume which is a minimum amount of tear volume a patient should have to be considered a candidate for the selected correction. For example, the first threshold value can be set at a tear volume level corresponding to a dry eye with a tear volume level so low that the measured tear volume level is a contraindication for LASIK refractive surgery. The first tear volume level can also be set at a tear volume level so low that the measured tear volume level is a contraindication for PRK. Software loaded on the processor can warn the health care provider not to treat the patient with the selected correction. A second tear volume threshold can be set to correspond to a minimum tear volume level at which the patient is a candidate for selected correction, is unlikely to have a delayed recovery. Such a patient can be diagnosed as category 3. If the measured tear volume level for the patient falls below the second threshold amount and above the first threshold amount, the patient may have delayed recovery for the type of treatment selected, and the patient can be diagnosed as category 2. Patients falling into this second group can be diagnosed as having potential side effects. Patients in the second group can be diagnosed as having potential side effects based on the comparison of the cornea to the depth of treatment at step 232, the comparison of pupil size to size of optical correction at step 234 and the comparison of the measured tear volume level to the second tear volume threshold at step 236. Patients in the second group can be diagnosed as being at risk for delayed recovery or be treated for dry eye before undergoing refractive surgery. Patient diagnosed as being at risk for delayed recovery can be warned, and the risk of the delayed recovery and the diagnosed condition of the eye noted in the patient chart. The delayed recovery can include a delayed recovery of vision, and a delayed recovery of dry eye symptoms and visual comfort. It should be noted that the values of the threshold amounts listed in steps 230-246 to select a candidate for refractive surgery can be different from the threshold amounts in steps 202 to 220 to diagnose and measure the eye.

After the patient has been screened and a treatment has been selected, the patient can be treated with the selected treatment. The patient can be monitored after treatment using the measurement techniques described above. A patient follow up schedule can be determined based upon what category the patient belonged prior to treatment. A patient in a category corresponding to possible delayed recovery can be placed on a follow up schedule providing a greater number of post-operative visits.

Figure 6C:
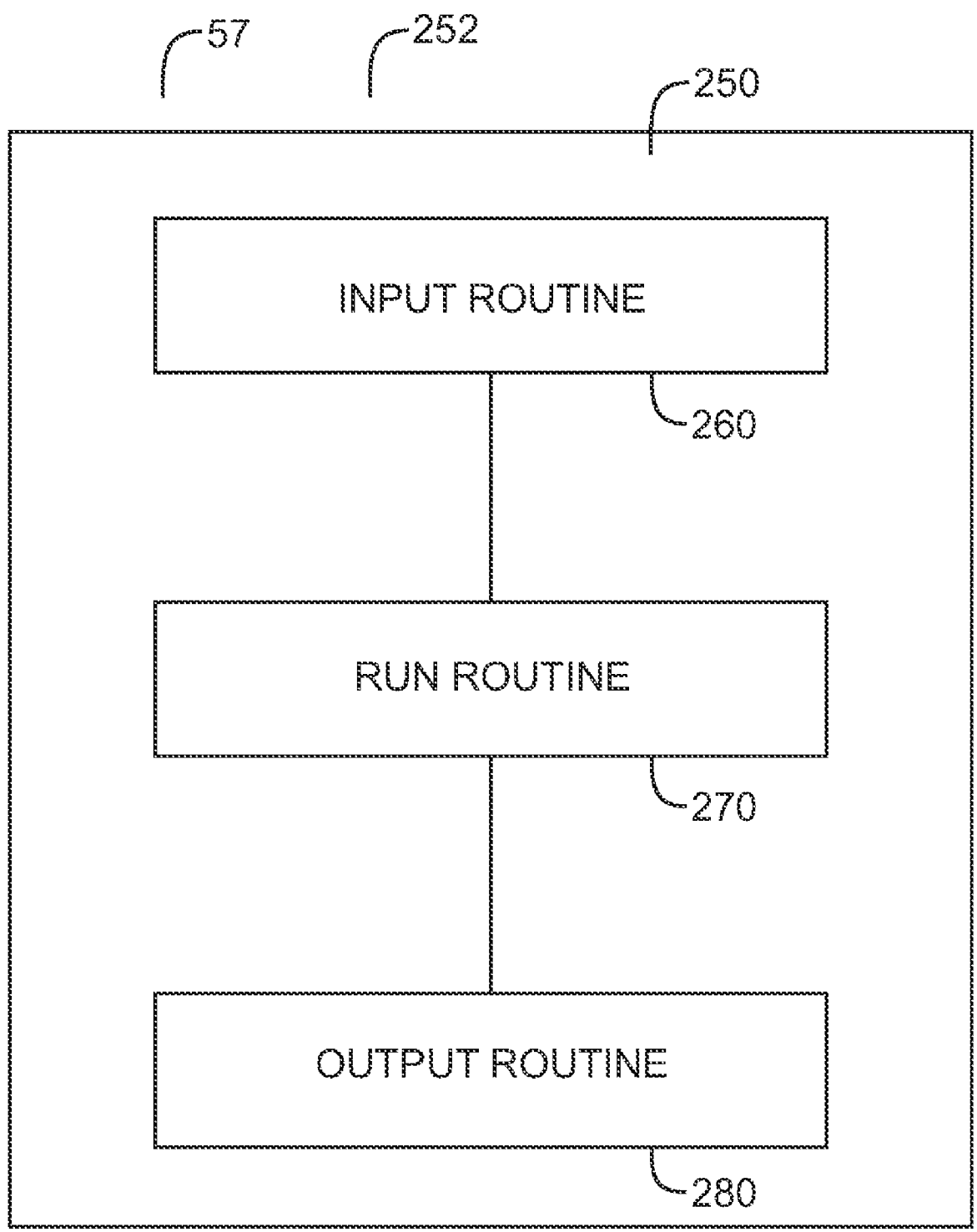
FIG. 6C illustrates a simplified flow chart of a computer-readable storage medium having a set of instructions that can be read by a computer to diagnose conditions of an eye.

FIG. 6C illustrates computer-readable storage medium 57 having a set of instructions 252 for a computer to perform the methods described in FIGS. 6A and 6B as shown above. Medium 57 can include a variety of tangible media as described above. In particular, the storage medium can be RAM which temporarily stores the set of instructions. This temporary storage can occur on a client computer or server computer or both, or a computer which is not connected to another computer with a network or the like. The set of instructions can be loaded onto the medium by any means including transferring set of instructions 252 from the Internet, the intranet, the LAN, the floppy drive, the CD ROM drive and the flash RAM such as a jump drive. The set of instructions can include an input routine 260, a run routine 270, and an output routine 280. Input routine 260 can be operatively associated with a source of sensor data. For example input routine 260 can cause the acquisition of measurement data from a CCD array as described with regard to steps 202, 204 and 206 herein, and read this data into the computer RAM. Alternatively, input routine 260 can read data from the tangible medium, the internet, an intranet, a LAN or the like, so as to make the data available for analysis. For example, measurement data acquired from the techniques 200 as shown in FIGS. 6A and 6B can be input with routine 260. Run routing 270 can process the data made available to the processor with input routing 260. Run routine 270 can use the acquired data from steps 202, 204 and 206 to diagnose the eye as described in steps 208 to 220. Alternatively or in combination, run routine 270 can diagnose the condition of the eye as described steps 230 to 246 in FIG. 6B using any of the data made available by input routine 260. After the condition of the eye has been diagnosed, an output routine makes the condition of the eye available for external use outside the computer. For example, output information 80 can be shown on the visual display as described above with reference to FIG. 5.

While the exemplary embodiments have been described in some detail for clarity of understanding and by way of example, a variety of additional modifications, adaptations, and changes may be clear to those of skill in the art. Hence, the scope of the present invention is limited solely by the appended claims.

What is claimed is:

1. A system for evaluating an eye of a patient, the system comprising:
    a first detector capturing wavefront or topography measurements from the eye when the eye is at an eye measurement location;
    a second detector capturing an image of the eye when the eye is at the eye measurement location, the image comprising a lid of the eye and a tear fluid meniscus extending along the lid;
    an optical train forming the image comprising the lid and the tear fluid meniscus extending along the lid; and
    a processor coupled to the first and second detectors, the processor determining optical characteristics of the eye and measuring tear volume in response to the tear fluid meniscus extending along the lid.

2. The system of claim 1 wherein the processor diagnoses the topography or wavefront of the eye with the image of the eye.

3. The system of claim 1 wherein processor registers a refractive prescription derived from the topography or wavefront with the eye using the image.

4. The system of claim 1 wherein a portion of the optical train is disposed between the eye and the first detector to capture the wavefront or topography measurements.

5. The system of claim 1 wherein the optical train is configured to form the image of the meniscus with a dark band corresponding to the meniscus.

6. The system of claim 5 wherein the processor is configured to determine the tear volume in response to the dark meniscus.

7. The system of claim 1 wherein the tear volume corresponds to a dimension across the meniscus of the tear.

8. The system of claim 1 wherein a first group of pixels of a sensor array comprises the first detector and a second group of pixels of the sensor array comprises the second detector.

9. The system of claim 1 wherein the processor determines a size of a pupil formed in an iris of the eye.

10. The system of claim 1 further comprising:
    a lenslet array passing light energy to the first detector, the first detector comprising a first array detector;
    a lens passing light energy to the second detector, the second detector comprising a second array detector; and
    wherein the processor determines a wavefront elevation map from the light energy measured with the first array detector and determines a dimension across the meniscus from the image captured with the second array detector.

11. The system of claim 1 wherein the first detector captures the wavefront or topography measurement in response to a user generated signal, and the second detector captures the image of the eye in response to the user generated signal.

12. The system of claim 9 wherein the first detector captures the light wavefront or topography measurement within one second of the second detector capturing the image of the eye.

13. The system of claim 1 wherein the processor diagnoses a condition of the eye comprising an irregular cornea, pyterigium, tear deficiency or lipid abnormality.

14. The system of claim 1 wherein:
    the processor generates a signal in response to tear volume below a threshold amount.

15. A computer-readable storage medium comprising a set of instructions for a computer to diagnose an eye with a tear volume and a wavefront or topography of the eye, the eye comprising a lid and a tear fluid meniscus extending along the lid, the set of instructions comprising:
    an input routine operatively associated with a first source of wavefront or topography data and a second source of tear volume data, the second source of tear volume data comprising an image of the lid and the tear fluid meniscus extending along the lid;
    a run routine diagnosing the eye with the wavefront or topography data and the tear volume data; and
    an output routine providing the diagnosis of the eye available for external use outside the computer.

16. A system for evaluating an eye of a patient, the system comprising:
    a first detector capturing wavefront or topography measurements from the eye when the eye is at an eye measurement location;
    a second detector for capturing an image of the eye when the eye is at the eye measurement location, the image comprising a lid of the eye and a tear fluid meniscus extending along the lid;
    an optical train forming the image of the lid and the tear fluid meniscus extending along the lid; and
    a processor coupled to the first and second detectors, the processor determining optical characteristics of the eye and measuring hydration of the eye in response to the tear fluid meniscus extending along the lid.

* * * * *